United States Patent
Wang et al.

(10) Patent No.: US 11,236,358 B2
(45) Date of Patent: Feb. 1, 2022

(54) METHOD FOR CREATING NEW GERMPLASM OF MALE STERILE CROP BY GENE EDITING AND APPLICATION THEREOF

(71) Applicant: JIANGSU ACADEMY OF AGRICULTURAL SCIENCES, Nanjing (CN)

(72) Inventors: Yinlei Wang, Nanjing (CN); Tongmin Zhao, Nanjing (CN); Wengui Yu, Nanjing (CN); Liping Zhao, Nanjing (CN); Rong Zhou, Nanjing (CN); Liuxia Song, Nanjing (CN)

(73) Assignee: JIANGSU ACADEMY OF AGRICULTURAL SCIENCES, Nanjing (CN)

( * ) Notice: Subject to any disclaimer, the term of this patent is extended or adjusted under 35 U.S.C. 154(b) by 86 days.

(21) Appl. No.: 16/612,764

(22) PCT Filed: Sep. 20, 2018

(86) PCT No.: PCT/CN2018/106586
§ 371 (c)(1),
(2) Date: Nov. 12, 2019

(87) PCT Pub. No.: WO2020/006885
PCT Pub. Date: Jan. 9, 2020

(65) Prior Publication Data
US 2021/0115470 A1  Apr. 22, 2021

(30) Foreign Application Priority Data
Jul. 6, 2018 (CN) .......................... 201810735328.6

(51) Int. Cl.
*C12N 15/82* (2006.01)
*C12N 9/22* (2006.01)
*C12N 15/11* (2006.01)

(52) U.S. Cl.
CPC ........... *C12N 15/8289* (2013.01); *C12N 9/22* (2013.01); *C12N 15/111* (2013.01); *C12N 15/8213* (2013.01); *C12N 2310/20* (2017.05)

(58) Field of Classification Search
None
See application file for complete search history.

(56) References Cited

U.S. PATENT DOCUMENTS

2015/0067922 A1* 3/2015 Yang ................. C12N 15/8273
800/298

FOREIGN PATENT DOCUMENTS

| CN | 106048089 A | 10/2016 |
|----|-------------|---------|
| CN | 106929532 A | 7/2017 |
| CN | 107667853 A | 2/2018 |
| CN | 108130328 A | 6/2018 |
| WO | 2017062756 A1 | 4/2017 |
| WO | 2018035300 A1 | 2/2018 |

OTHER PUBLICATIONS

Lapidot et al. 2015 (PLoS Genetics 11:10, p. 1-19).*
Yang Shao-Hua, Chen Hui-Mei, Zhou Shu-Fen; CRISPR/CAS9-mediated Editing for Pollen-Spesific OsIPA Genein Rice; Fujian Journal of Agricultural Sciences; 2017; 1173-1177; 32(11).
Hai Zhou, et al. Development of Commercial Thermo-sensitive Genic Male Sterile Rice Accelerates Hybrid Rice Breeding Using the CRISPR/Cas9-mediated TMS5 Editing System; Nature; Nov. 2016, vol. 6, pp. 1-12.

* cited by examiner

*Primary Examiner* — Matthew R Keogh
(74) *Attorney, Agent, or Firm* — Bayramoglu Law Offices LLC

(57) ABSTRACT

A method for creating a new germplasm of a male sterile crop by gene editing and an application thereof are provided. In this method, the gene editing is performed on an exon region of a Ty-5 gene, and a deletion of DNA sequence is introduced by using a repair mechanism of plants themselves to double-strand breaks (DSBs), causing a loss of function of Ty-5 gene, thereby obtaining a male-sterile character. The method can be applied without being limited by crop categories. After the gene editing is performed on Ty-5 genes of various crops, new germplasms can be quickly obtained. The new germplasms have the same agronomic characters as the previous materials, and only differ in sexual aspect, which effectively solves the problem of the lack of male sterile materials and unstable fertility in natural resources.

2 Claims, 2 Drawing Sheets
Specification includes a Sequence Listing.

SEQUENCE LISTING

```
<160> NUMBER OF SEQ ID NOS: 7

<210> SEQ ID NO 1
<211> LENGTH: 7740
<212> TYPE: DNA
<213> ORGANISM: Unknown
<220> FEATURE:
<223> OTHER INFORMATION: The full length sequence of the Ty-5 gene in
      the tomato material moneymaker

<400> SEQUENCE: 1
atgaagattg ttcgtagaga ctttgttcct gatggttctg gtagtgtaaa ggtaactttt        60
ttatctctat aattgttgtt taaatctata attcgagtaa ttttcgtgat tttttgaaac       120
cccagatgaa gaaaacgtta aaattgattt gggtattttt tatttttttaa ttttcatgtg       180 ttatacagat aattccagaa gaagctgatg atctatgggt tgcttataat ctgatagctg       240
aaggtgatac tgtattagct gttactgtta ggtattgcac ttttgctcaa ttttattagt       300
gtgagggctt agcattatta gcaatttttt tgggataaat aagtaatttt tattcgcgta       360
tgtaataagt ttgagatttt gtagaaaaac atgtttttac tataagaagc atttagttta       420
tactactccc ttactccgtt acaatttgtt tgtttggttt tgaattgtca cgagtttttt       480
aaaaaagaga gtaaagaacg acttttgaat ctcatggtct taaactaaa gagattgtgg        540 gatgtacgga atttggtctt ttatcttgtg ctattaaata tggtaggtgg aaagtcgaat       600
agaagagttg ccaaataagg aaagagacat tattttttgga acaaactaaa aagaaaagta       660
ggataaacaa attaaaacag ggggagtatt tggtttctca tcggtgctac aagaattact       720
aaaaagctag cgtcttgcct tttttaaaaa gaaatttttga tcctgaaaga tggagttttt      780
aatttgaata tggatgtcac ttgctaatta ggttcgaatt ctgttcattc gaaagcttgg       840 agcttttttac tttgtttata actacatagt tgattctcta cacttgttaa tgtttctcat      900
cctgttgagt tgattgaaaa tttatgttttt ttggataaca tattaattgc tctcgttctc      960
gtaaatgtct aatttctgca tcaattttttg ttgtttttatt cgttgattag ctaattctta    1020
gaaaatgtag tgttctgtga tgtgcgaaag taatctataa atagttagac tctaatcaga      1080
tttgtgctaa attctagtta aatttgtcta aattggcctg agatgagttt atataaactg     1140
tggagttaca tggtcagtga ggattcattt atacgacctg aacttgcttg gactgaggtg      1200
```

-continued

```
ttgttgttat tgttgtttgc tgaaattgtg aatgacaatg ttactataag gaaaatggat    1260
tttgagcata gtgtgagtct ctactgatta cacaggttga taatagtatt gttatatttg    1320
ttttgcttaa agcttagggg aagactcttt tttaatgttg agagcaactt tcttttgcaa    1380
attatgctat gtgggtcttt gctgattgtt aacacggttt agcttgtcac aacacaacct    1440
actggaagct ggttaaattt tgcttgtaat ttcttgtagg aaggtcctga gggaagctgc    1500
ttctggagga agagatgctg aacgagtgaa actgaaattg gaaattaaag ttgaggtaag    1560
gatatattag acatccagca tcattcagtt gtggggtgcg ggccttggtt agaactttgt    1620
tttagcttcc agcataaggt gttttaatat aaattgaaag ataaaacttt gaatcaatt     1680 aactatagag aagaatctac taaggataga gaggagactt ttctttgtct tccttttcca    1740
atgtggtcga gatgaagtat ttttgggcag tttgatgaat tttgaggata tcaatacaac    1800
ccgtgtatga catatgcatg ataaattgtc acataacaat gctccatttc taactaatct    1860
caataaatgc gatgttgata gttttgttac catagtaatg atgacaattg taatgtgact    1920
ggaaagtagg aaatagatag tgctctttct agagttttta tttgaatata ttccactcca    1980
atgtggtata atataatcaa tttggtgttt tagaatgtgg agtatgacaa agaaggttct    2040
gccttgcgta ttcgcgggaa gaatattctg gagaatgaac atgtaaaggt gtgtattctt    2100
caacttaatc cttttggata aattcctaat attgatgctg caacaaaaat gtatctaatt    2160
attttattgc agatagggc cttttcacact ctggaaattg agcaacacag accttttgtg    2220
ctaagaaagg tacaatgctg tgttttgatt cttttgcaac tatcactctg ttttcttttta   2280 aaaattttga ggtatattat ttgcacttta aaagctatca agctggtgat atatgttctt    2340
taggattgca gctctaacct atgtttctca gactcttcaa aaatgtcaac tggtgcatgt    2400
cggattctcc aaaaatagcg tgttttggaa tatccgacat gggtgcggca ttgtaagtga    2460
agagtccgca acttaggctc taacaagtaa aaaaatctgt aaagttattc atgtaattta    2520
cattattatt ataaaatccc cggaaaaaga agaagagtac cttttttttc tttaataacc    2580
ttggtatccg ggccagtttg tgcacacttc gaccacttcc accaacacag ctaccgccta    2640
cagggtaact ctttccatca aggttttgac aaataagaag aaattgtcta gtgttttcg     2700 cctctggttg gatttgaacc taagatctta tgactcttaa ctcacttcat tggccgctag    2760 accataccc ttgggtgcag ttacttgaaa ctaagtttaa ttttttcccgc taaatttcag    2820 ttgtcccgcc gctgacaccc cttcgaggca tctcgtgttc ctgtccttg acgtagttca     2880 catcctgcac gaaaggtgta catacgatac ctcctttctg tctctagatg gaacaacct     2940 tctacattaa tgatgattcc accttggtta tcatcatgac taattccatg ccaaataagc    3000
caagaaatag ctacacattt tcggcacaca ccaaaaaagg gaacccgaag tatattgtcg    3060
ttgatttctc ataaacaagt gtacaatggt tcgaaaatta tccgaaagca ttaatgctta    3120
ttaagctatt attaactcct atattataca ttctatggac tttggtctga gggggctagt    3180
ttcttttctc agcttgtttc tttgtagttt gaaggatcta tgcccctag ttcgtccaac     3240 acaggtaggg ctgaggcatg ataagataag tgacggtttg tgtagcctag gtaatatata    3300
cttaagtgat gcaacaatat aagttcaggt agggaaatt cttctcgtac acataggagt     3360
acatggaatt tggtaagatt tcttgatttt tttctgcatt atacaaagtt gctgcataga    3420
ttaagtataa ctaaataagt gtcttttttat aattagaggc taatgagtca tagaagttga    3480
attaggagat aatcatttgt agttgtaact agaggtttct ataggaaatt gaggagtatc    3540
```

```
ccaatcgaaa tataaatgcc taaaaatgtc tgggctaaga attacatgtg aacttgatgt    3600
ctgggctaag aattacatgt gaacttgaaa ttatattgat cgggtacagg tcgaatgaaa    3660
ttttccataa tttcttttac tactggattt attacttaaa agggtataaa cttatcaaaa    3720
taagatttct tagaaggtat gcgtgctttt atttaaaact tttgtttatg tataatccta    3780
tctaatgcat gtacatgaat tattttgaat ttatttttac tcaaagtaat cgttattttc    3840
ctgtgtcatc ttccttatta ttttttgtata ttctatttgt ttagcaaata tatgagcatc    3900
ttgtttgttt caatcttagt cttacctgaa catagttgat ttatacgaaa gcttatacat    3960
atatgagttc tgacttgcat tatctgattt aggtggtctg ggactcactg gcacgggagg    4020
ttcttcgtca agcttctggt attttttcaca gtgcacttta acaaagttat attttttattt    4080
gttcaagtgt tgccattaac tttatctgca atattaggca ttttagttca tagcctgact    4140
tttcatccat aacttatcaa gttctataac atgttgctgc ttcttttttag tacattgaca    4200
tgattgtgaa accactttat aggtgcatta ttcttagatg gattgtttca gtctaggtgt    4260
cttttagccc ttatgttgca gaggttttct tctttactcg tacacttgca gtgagaacat    4320
gattattcgc tgcaagtaca tgtgtgttgc agagtgcttt tgaactgatg agaagttttcc    4380
tatataattg ttgatattca gctatattga ttccaacatg gatatgtgtt tgtaactttg    4440
tactgctctt agatttaccg tttcaatatg ctgaatacgg ttttccttt tgatgattca    4500
gatccatctg caagtgctga tctggctgtg gttctgatgc aagaaggatt ggcacacatt    4560
cttcttattg gtaaaaggta agcttgacaa tctcatagtc ctatgaatac aagttttaaa    4620
cagatcttga gcatctcctt ttcttgtatt taaacgagat gtaatagttt aaaagtcgaa    4680
tgattatgtc agaatttcta tatgttgagg ctgagttaag tgttaactag attgtatggc    4740
ataatttttac cttatgtact tgttactgtt gtctgaacag tgtgactatc acccgttctc    4800
gtatagagtc ttctataccg cgcaagcatg gaccggctat tgcaggttat gataaggtga    4860
gtctcttact tcttttttgtt tcatcttttg tataatttaa ttattttgaa catgacgtca    4920
agtgaaattg tgttcttaat tttgatttgc aggcgttaaa taaattcttt gacaatgttc    4980
tacaggtaga cttttgtcaa ctttcttgat gttgcttaat ttccagaagc aatatgttat    5040
aggttcttat ttctgttgca ggcctttgtc aagcatgttg atttcaaagt agttcgctgt    5100
gctgtgattg caagtccagg attcaccaag gtattttttg tatagttaca cttcttagct    5160
agtcatactt ttatgctatg ttacaagggg tagaacttgc atatctaatt atatctgtac    5220
tatgcatatg ttaattcagt tgtgacattt aaacttttt tgtgttgaatg tgcaggatca    5280
gtttcatcgt cacctgttgt tggaagccga gaggaagcaa ctaagaccta aatagaaaa    5340
taagtcacgc ataattcttg tccatacaac ctcgggatac aagtatgccc ttctttctct    5400
ctctccttgc ccttcatctg acatctcaaa acgagtcaat acatttttgt gcaaaccata    5460
tgatgttaga catgcgtgct agtctaaaat tgactaatat gtagcaatac attttgtgt    5520
acgcgattct ctcgtcagta ctgctatttt agtacaaatc gcctttatta tttgtctatt    5580
gtagttgata tgtaaaagtt caattattat ccagcacggg tgtttaaggc cgagagtttt    5640
ttttttcccct cgttttacag acatagtttg aagagggtta tggatgcccc aaatgtaatg    5700
actatgataa aagatacaaa agctgccaaa gaggtaccct ctgacccttg tccaacttga    5760
tatgatcttt aatctttatt cttgtgtttg ttcaagtctt ttttcgtatt ttttgggaat    5820
aactgttttc ctttctcttc caatcttaat caggttcaag ccctaaagga ttttttcaac    5880
atgctttcaa atgttaggtt ctatccttgg tctcaatgtt ctatttatat ttttcttaat    5940
```

-continued

```
aactttggat gtttcagatt tttatctatc atatgctaag agtaaacaca gattgtttgg    6000
ttttgaattt atttgtttgc ttttttttggt gtttatcggt tatcttgggt tctgtaagag    6060
gcctgagagt ttcaaataaa agtttgaggt gtttaactat gcatgacgga tatccctgtt    6120
taaggagagg tggactaatc tgaaatattt ctagattaag aacagatacg ttgtgttatg    6180
atgggcagct ggtgatattg ttatctctgc gtgtgccttt ttttaggcct ttctaccaat    6240
tgaatgctga aaattcattt gcaaccaacc ttggttgaat ttattttcag caaggatccg    6300
tcataattct cagatatcca atcatcaaca actttgaact tctattaaat tttagggcat    6360
ctcagttgtg ttcttttcatc ttttgatttt atatgcaatt ttactgtagt aataggagta    6420
tctctcttca atgctttggc catatcggta cgagagaatt tatcatctga tgtgccctct    6480
cctttacttt tttgcagaca gaaaatacga taaggaagtc ttaattaaaa atatgcgtgt    6540
gcttgatttt ctggttttaa ggatatttag gtctaaaaac tatagttaca ttacataatt    6600
tagggatgct agatgtagag gtcttttgct agagcgagtg cttgtttgaa ccccccgccc    6660
cgccccgcat atttcatgaa ttatgatatt aattggatat ttatgatacc gcttttcaag    6720
ctttctgaag aaactaagaa ggataacatc tttatttaaa aacttttttc cctctcttgt    6780
tataacttct tgcaataaat gtagtcatgt ccctttttct ggatctctta acatttatat    6840
taatgagccc ctgcatgaag tttacttcca gttgtcaaca aatagatcct tgtagtgtgt    6900
ttctttaccc gaaacttgtg aaaattgaag ttactttatt tggacttctc taggatcctg    6960
atcgtgcatg ctatggacca aagcatgttg aagttgccca tgagcgtctg gctattcaga    7020
cacttctcat tactgacgag ctctttaggt gagtatctta tggtcccagg ttaatggggg    7080
ctttatgagc aataaaatta aactgtatat agcttgatat aaatttgcaa ctcgtggcat    7140
atttcaagtt cataagtatc tcttttttacg tgcttagctt ttaaaatcga catctttggt    7200
tcataggata atatgtaaac atgtataact atcttcaaat ctcaaccagt tatgtatggg    7260
ccatttcact cgtgctgtat atatatagtt ggttgatatc gtacatgaga aatatccaac    7320
ttcttttgat ctgttgacag gagttctgat gtagaaacga ggaaaaagta tgctaatttg    7380
gtcgattcag tcaaggattc aggtggtact gctctcattt tctcgtcaat gcatgtctcc    7440
ggagaacgtg agtatataca attcctgtta atttcttttt cctcccagca ttttcatctc    7500
tgcctttccc tgtcgccccc tagtaatgct tagaatggta ttttccttct gtgcacatat    7560
tcattgtccc atagtcgctt caaatccttt ttccttccta cgaacacacg ttctttactg    7620
catatttgtc aaggctgatt aaaacaactt ttggttttcg tcacagaatt gaatcagcta    7680
accggcattg ctgcaatcct tcgttttcct ttgccggagc tggaagacat tgagatgtga    7740
```

<210> SEQ ID NO 2
<211> LENGTH: 19
<212> TYPE: DNA
<213> ORGANISM: Artificial Sequence
<220> FEATURE:
<223> OTHER INFORMATION: Target sequence

<400> SEQUENCE: 2
agaagaagct gatgatcta        19

<210> SEQ ID NO 3
<211> LENGTH: 22
<212> TYPE: DNA
<213> ORGANISM: Artificial Sequence
<220> FEATURE:

-continued

```
<223> OTHER INFORMATION: Primer: Target-F, designed based on the target
      sequence

<400> SEQUENCE: 3
ttgagaagaa gctgatgatc ta                                              22

<210> SEQ ID NO 4
<211> LENGTH: 22
<212> TYPE: DNA
<213> ORGANISM: Artificial Sequence
<220> FEATURE:
<223> OTHER INFORMATION: Primer: Target-R, designed based on the target
      sequence

<400> SEQUENCE: 4
aactagatca tcagcttctt ct                                              22

<210> SEQ ID NO 5
<211> LENGTH: 24
<212> TYPE: DNA
<213> ORGANISM: Artificial Sequence
<220> FEATURE:
<223> OTHER INFORMATION: sequencing primer: sqprimer

<400> SEQUENCE: 5
gatgaagtgg acggaaggaa ggag                                            24

<210> SEQ ID NO 6
<211> LENGTH: 23
<212> TYPE: DNA
<213> ORGANISM: Artificial Sequence
<220> FEATURE:
<223> OTHER INFORMATION: Amplification primer: CRISPR5-F

<400> SEQUENCE: 6
tccattgaac tgaagcaaat ctc                                             23

<210> SEQ ID NO 7
<211> LENGTH: 23
<212> TYPE: DNA
<213> ORGANISM: Artificial Sequence
<220> FEATURE:
<223> OTHER INFORMATION: Amplification primer: CRISPR5-R

<400> SEQUENCE: 7
gctaataatg ctaagccctc aca                                             23
```

METHOD FOR CREATING NEW GERMPLASM OF MALE STERILE CROP BY GENE EDITING AND APPLICATION THEREOF

CROSS REFERENCE TO THE RELATED APPLICATIONS

This application is the national phase entry of International Application No. PCT/CN2018/106586, filed on Sep. 20, 2018, which is based upon and claims priority to Chinese Patent Application No. CN201810735328.6, filed on Jul. 6, 2018, the entire contents of which are incorporated herein by reference.

TECHNICAL FIELD

The present invention belongs to the technical field of gene editing technology for crop breeding, and particularly relates to a method for creating a new germplasm of a male sterile crop by a gene editing and an application thereof.

BACKGROUND

Crop male sterility is a phenomenon of normal pollination failure due to inability to produce pollen or abort pollen, which is caused by abnormal male organs resulting from physiological or genetic reasons of sexually propagated crops. Because crop male sterility can avoid the artificial emasculation in the pollination process in crop heterosis breeding, a lot of labor input is saved. Meanwhile, crop male sterility significantly improves the purity of hybrid varieties, and creates varieties with heterosis.

Male sterility technology plays an important role in the utilization of heterosis, and obtaining stable male sterility materials has important application value. Male sterility can be divided into nucleus male sterility and nucleus-cytoplasmic male sterility according to a genetic model and position of male-sterile character in cells. At present, male sterility has been applied in crops such as rice, corn, wheat, cabbage, pepper and the like. However, in many crops, male sterility is not used for production mainly due to problems like lack of male sterile resources and stability of male-sterile character of male sterile materials. It is found that the male sterile line material with natural mutation is the main source of male sterile materials. In addition, male sterile materials can be obtained by distant hybridization, artificial mutagenesis, and cell engineering. With the development of biotechnology, it has become possible to create male sterile materials through genetic engineering.

The gene Ty-5 is a tomato yellow leaf curl virus resistance gene in tomato, and is also a surveillance factor for monitoring a peptide chain synthesis process. The gene Ty-5 exists in all crops. In the present application, the new germplasm of male sterility can be created rapidly by performing a gene editing on the gene Ty-5. The development of gene editing technology provides a powerful weapon for the utilization of Ty-5 gene in heterosis breeding. The current gene editing technologies mainly include zinc finger nuclease technology, transcription activator-like effector nuclease technology, and the latest CRISPR/CAS9 gene editing technology. Gene editing realizes the recognition and cleavage of specific DNA sequences, and the introduction of different types of mutations such as deletion, substitution, and insertion of bases at double-strand breaks (DSBs) of DNA, achieving fixed-point editing of DNA.

SUMMARY

In view of the problems of the shortage of male sterile materials and the low purity of hybrid varieties, and the current situation of long time and high cost of conventional breeding, gene editing technology is applied to Ty-5 gene according to the present invention, so as to rapidly create a new germplasm of a male sterile crop while retaining agronomic characters of an original male fertile material.

In order to solve the above technical problems, the following technical solutions of the present invention are used.

(1) All of the existing gene editing methods can be used for the editing of Ty-5 in this study. In the present invention, only CRISPR/Cas9 technology is used for the gene editing of Ty-5. A deletion of DNA sequence is introduced by using a repair mechanism of plants themselves to DSBs, causing a loss of function of Ty-5 gene, thereby obtaining a male-sterile character;

(2) gRNA target sites are selected in an exon region of Ty-5 gene. According to the principle of CRISPR/Cas9 target anchor, the 18-20 bp upstream of the protospacer-associated motif (PAM) as the target site, i.e., (5'-N18-20NGG-3', NGG is a PAM sequence, and N18-20 represents a recognition sequence of 18-20 bp);

(3) Oligo sequence primers are designed based on the recognition sequence:

```
Target-Sense:
5'-TTG-NNNNNNNNNNNNNNNNNNNN (N represents gRNAsense
sequence)

Target-Anti:
5'-AAC-NNNNNNNNNNNNNNNNNNNN N represents the
reverse complement of gRNA sense)
```

The primers are respectively diluted to a concentration of 10 µM, 5 µL of each of the above primers is taken, and 15 µL of water is added for a uniform mixing to form a mixed solution. The mixed solution is placed at 95° C. for 3 minutes, then slowly cooled to 25° C., and finally kept at 16° C. for 5 minutes to complete a synthesis of an oligo dimer;

(4) A CRISPR/Cas9 kit VK005-14 from VIEWSOLID BIOTECH, Beijing is selected, 1 µL of synthesized oligo dimer, 1 µL of Cas9/gRNA vector, 1 µL of Solution 1, 1 µL of Solution 2, and 6 µL of $H_2O$ are mixed uniformly to form a mixed solution, and a reaction is performed on the mixed solution at 16° C. for 2 h;

(5) After ligation, the vector is transferred into *E. coli* competent state, a single clone is picked for plasmid sequencing analysis. A sequencing primer is sqprimer: 5'-GATGAAGTGGACGGAAGGAAGGAG-3', and a positive plasmid is transferred to *Agrobacterium* GV3101;

(6) A cotyledon of the crop is used as an explant, a plant regeneration is carried out by a leaf disc method, *Agrobacterium* GV3101-mediated transformation is performed, and a regenerated plant is obtained by hygromycin resistance screening;

(7) Primers that can amplify the target site are designed according to upstream and downstream sequences of the target site, and the regenerated plant DNA is extracted to be used as a template for PCR amplification. The amplified products are sequenced, and a sequencing analysis is performed on the regenerated plants to determine whether a gene editing occurs and whether an editing type is homozygous mutation;

(8) After the sequencing analysis, a pollen content and germination identification is performed on homozygous gene edited strains. The results show that the homozygous edited Ty-5 plants created by the gene editing are new male sterile germplasms.

Compared with the prior art, the advantages of the present invention are as follows:

(1) The method for creating a new germplasm of a male sterile crop of the present invention can be applied without being limited by crop categories. After the gene editing is performed on Ty-5 genes of various crops, new germplasms can be quickly obtained. The new germplasms have the same agronomic characters as the previous materials, and only differ in sexual aspect, which effectively solves the problem of the lack of male sterile materials and unstable fertility in natural resources.

(2) As compared to a conventional breeding method, materials treated by the method of the present invention can obtain male-sterile characters more quickly.

(3) As compared to a conventional breeding method, materials treated by the method of the present invention can better retain the agronomic traits of the acceptor material.

(4) The new male sterile germplasm created by the present invention is a powerful supplement to existing materials.

(5) Performing a hybrid seed production by using the materials created by the male sterility creating method of the present invention can greatly reduce the labor requirement and improve the purity of the hybrid seed.

Figure 2:
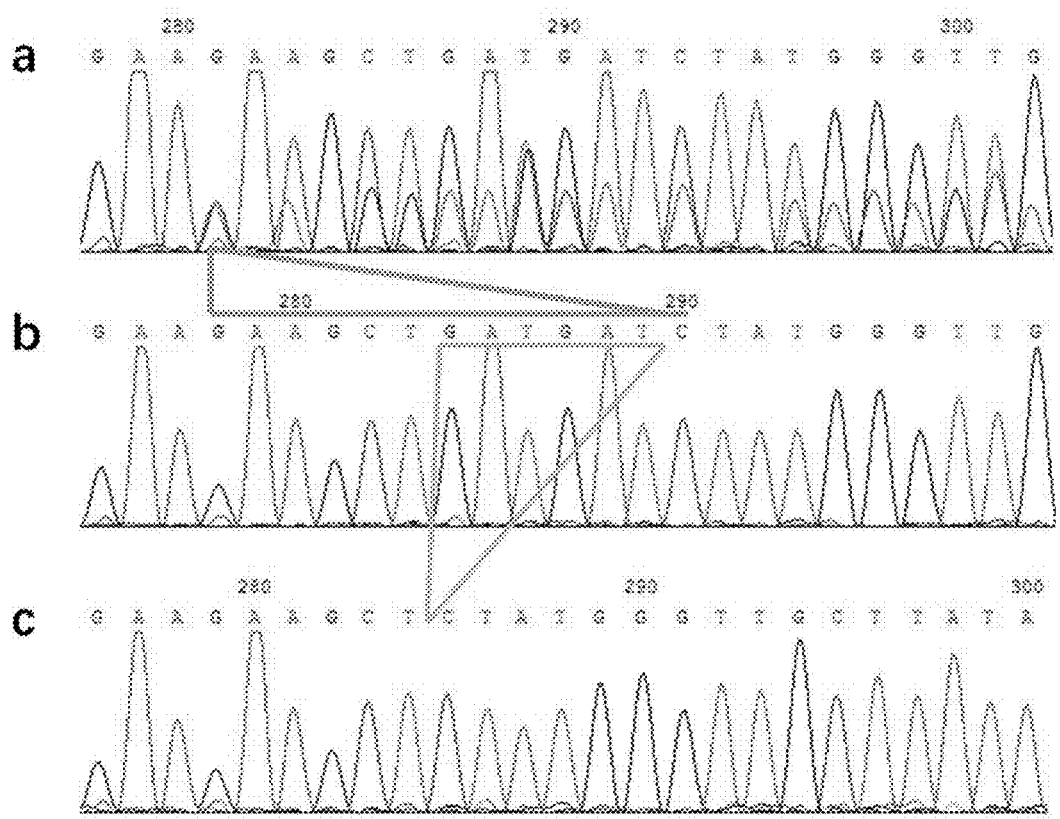
Figure 3:
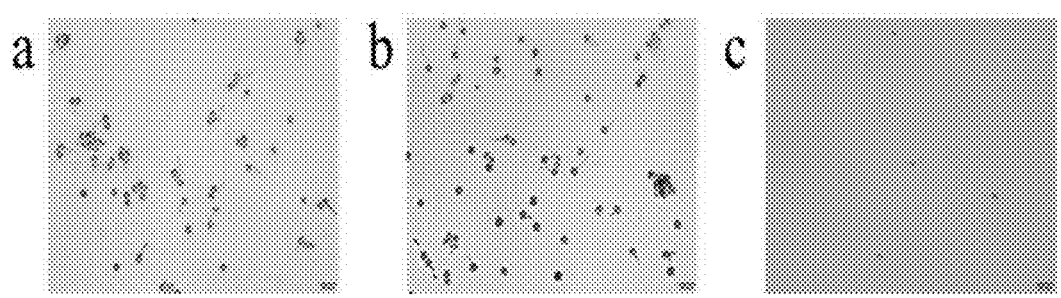

(M: 100 bp Marker; 1: regenerated plant No. 1 after the gene editing; 2: regenerated plant No. 2 after the gene editing; 3: wild type Money maker material);

FIG. 2 is a diagram showing results of a sequencing of each material band amplified by a CRISPR5-F primer;

(a: regenerated plant No. 1; b: a sequencing result of a wild type moneymaker; c: regenerated plant No. 2; triangle boxes indicate sequence deletions of the regenerated plant No. 1 and the regenerated plant No. 2, respectively); and FIG. 3 is a diagram showing a comparison of pollen germination;

(a: regenerated plant No. 1; b: wild type moneymaker; c: regenerated plant No. 2).

DETAILED DESCRIPTION OF THE EMBODIMENTS

The technical solutions of the present invention will be clearly and completely described with reference to the drawings in the embodiments. It is obvious that the described embodiments are only a part of the embodiments of the present invention, but not all embodiments. All other embodiments obtained by those of ordinary skill in the art based on the embodiments of the present invention without creative work should be considered as falling within the scope of the present invention.

A method for creating a new germplasm of a male sterile crop through a gene editing, includes the following steps:

(1) Materials

Material of moneymaker having normal stamen fertility;

CRISPR/Cas9 Kit: a CRISPR/Cas9 Kit VK005-14 from VIEWSOLID BIOTECH, Beijing was selected;

T carrier: TransGen Biotech, Beijing. (CT301-01);

DNA Extraction Kit: TIANGEN Biotech (Beijing) Co., Ltd. (DP305);

*Agrobacterium* competent state: GV3101;

Primer synthesis and sequencing were completed by GenScript Biotech Corp. (Nanjing).

(2) Selection of gRNA Target Sites

The full length sequence of the Ty-5 gene (as shown in SEQ ID NO: 1) includes a total of 16 exons, and the second exon sequence was selected for the design of the gRNA target site in the present embodiment. The length of target sequence is 19 bp (as shown in SEQ ID NO: 2). The primers were designed based on the target sequence:

Target-F: 5'-TTG-AGAAGAAGCTGATGATCTA-3', as shown in SEQ ID NO: 3,

Target-R: 5'-AAC-TAGATCATCAGCTTCTTCT-3', as shown in SEQ ID NO: 4;

(3) Oligo Dimer Synthesis:

The Target primers were respectively diluted to a concentration of 10 μM, 5 μL of each of the above primers was taken, and 15 μL of water was added for a uniform mixing to obtain a mixed solution. The mixed solution was placed at 95° C. for 3 minutes, slowly cooled to 25° C., and then kept at 16° C. for 5 minutes, so as to complete the synthesis of oligo dimer;

(4) Construction of CRISPR/Cas9 Recombinant Vector and Transformation of *Agrobacterium*

The reaction system was as follows: 1 μL of synthesized oligo dimer, 1 μL of Cas9/gRNA vector, 1 μL of Solution 1, and 1 μL of Solution 2, and 6 μL of $H_2O$ were mixed homogeneously to obtain a mixed solution, and the mixed solution reacted at 16° C. for 2 h. The ligated vector was transformed into *Escherichia coli* competent Trans1-T1, and coated on a plate for placing overnight. A single colony was selected for extracting the plasmid, and a sequence analysis was performed on the plasmid. The sequencing primer was sqprimer: 5'-GATGAAGTGGACGGAAGGAAGGAG-3', as shown in SEQ ID NO: 5. The plasmid was extracted from the colony with the correct sequencing result, and transferred into the *Agrobacterium* GV3101 by a freeze-thaw method.

(5) Tomato Transformation:

The main steps were as follows:

Pre-culture preparation of explants: Cotyledons that had just emerged from the seed coat were selected for transformation. The cotyledons were cut and placed in 50-100 mL of MS liquid medium. The stalk ends and tips of the cotyledons were excised and placed in D1 medium, and the cotyledons were placed upside down for culture in D1 medium. The culture dish was pre-incubated for 2 days in a constant temperature culture chamber (16 L/8 D) at 24° C.

Co-culture: 5 μL of 0.074 M acetosyringone was added to each 10 mL of MS liquid medium, 5 mL of the MS liquid medium (+AS) was taken to wash *Agrobacterium* colonies, the bacterial solution OD600 was diluted to a concentration of 0.3-0.4, and the bacterial solution was added to the pre-cultured (2 days) cotyledons. After infecting the cotyledons for 8-10 minutes by *Agrobacterium*, the excess bacterial solution was removed. The cotyledons were transferred to the D1 medium containing filter paper. The cotyledons were inversely placed (the lower surface of the cotyledon faces upwards) for incubation at 24° C. for 2 days in the dark.

Screening: the sterile cotyledons were transferred to a 50 mL centrifuge tube, washed twice with sterile water, and washed once with +Car; the cotyledons were inversely placed (back up) on the differentiation medium 2Z, 20-30 leaves were placed per culture dish to ensure the growth space required for cotyledons. The double-layer sealing film was used for sealing, and a cultivation was performed at 24° C. for 10 days (16 L/8 D). On the tenth day, the cotyledons were transferred to fresh 2Z medium plates, and then subcultured every 2-3 weeks. The callus appeared after 2-3 weeks. The initial buds appeared within 4-6 weeks. When the buds began to appear, the explants were subcultured every 2 weeks, and the medium was 1Z selective medium.

Rooting: the shoots were picked from the explants and placed in a 100 mL sterile vial containing 40 mL of MMSV medium (containing 0.5 mg/L IBA, 15 mg/L hygromycin and 200 mg/L Timentin). Roots began to appear after cultured for around 2 weeks. When the plants grown large enough, the seedlings were transplanted into small plastic pots containing a mixture of vermiculite and soil, and watered with nutrient water. A total of 2 transformed tomato seedlings were obtained by tomato transformation.

6. Regenerated Plant Detection after Gene Editing:

Leaf DNA of two regenerated plants and wild type moneymaker materials were extracted separately, and the following amplification primers were used:

```
CRISPR5-F: 5'-TCCATTGAACTGAAGCAAATCTC-3', as shown
in SEQ ID NO: 6;
CRISPR5-R: 5'-GCTAATAATGCTAAGCCCTCACA-3', as shown
in SEQ ID NO: 7.
```

Figure 1:
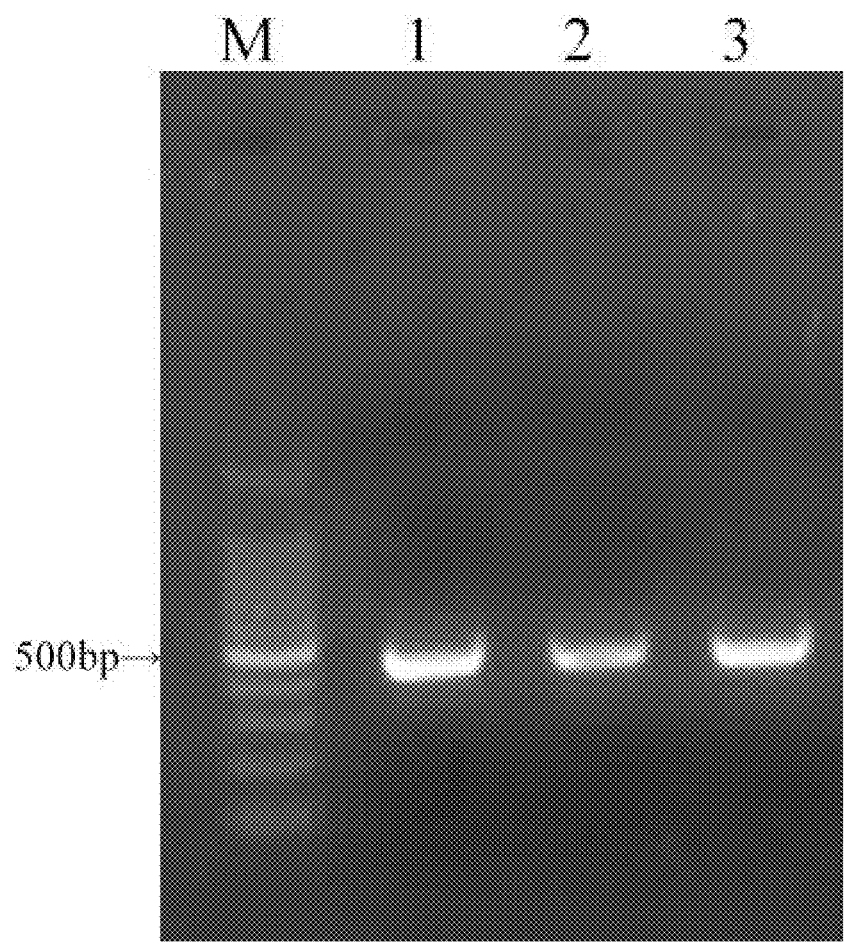
FIG. 1 is a diagram showing a regenerated plant after a gene editing amplified by a gene editing primer.

The length of the amplified fragment was about 450 bp, and the product after PCR amplification was subjected to an agarose gel electrophoresis to determine whether the size of the strip was correct (FIG. 1). The electrophoresis bands showed that the regenerated plants and wild type moneymaker materials could amplify a 450 bp band, and the three PCR products amplified by the regenerated plants and wild materials were sequenced by CRISPR5-F primers to detect the variation of the base sequence of the gene editing site (FIG. 2). The results showed that, as compared to wild type moneymaker materials, using the regenerated plants No. 1 and No. 2 resulted in sequence variation at the gene editing site. However, the variation type of the plant No. 1 was heterozygous mutation, and a 13 bp deletion occurred in one of the double-stranded DNA; the variation type of the plant No. 2 was homozygous mutation, and a 6 bp deletion occurred respectively at a same site of the double-stranded DNA.

7. Comparison of Pollen Content and Germination

The pollens of two regenerated plants and wild type moneymaker were collected, and incubated on the germination medium for 4 h at 26° C. in the dark. The pollen contents and the germination thereof of various materials were compared and observed under a microscope (FIG. 3). Through the germination comparison test, the pollen content of regenerated plant No. 1 was equal to that of wild type moneymaker, while the pollen content of regenerated plant No. 2 was significantly reduced. By the comparison of pollen germination, no pollen germination was observed in plant No. 2 after cultured for 4 h, but pollen germination was observed respectively in regenerated plant No. 1 and wild type moneymaker. It can be seen that homozygous variation (plant No. 2) can greatly reduce plant pollen content and stop pollen germination.

In summary, the present invention provides a method for creating a new germplasm of a male sterile crop by a gene editing. Through performing a gene editing on the Ty-5 gene exon region, the homozygous edited plant was obtained, which is a new male sterile germplasm.

SEQ ID NO: 1

The full-length sequence of the Ty-5 gene in the tomato material moneymaker, the underlined sequence is the intron sequence, and the shadow indicates the gene recognition site.

```
ATGAAGATTGTTCGTAGAGACTTTGTTCCTGATGGTTCTGGTAGTGTAAAGGTAACTTTTTTATCTCTATA

ATTGTTGTTTAAATCTATAATTCGAGTAATTTTCGTGATTTTTTGAAACCCCAGATGAAGAAAACGTTAAAATT

GATTTGGGTATTTTTTATTTTTTAATTTTCATGTGTTATACAGATAATTCCAGAAGAAGCTGATGATCTATGGG

TTGCTTATAATCTGATAGCTGAAGGTGATACTGTATTAGCTGTTACTGTTAGGTATTGCACTTTTGCTCAATTT

TATTAGTGTGAGGGCTTAGCATTATTAGCAATTTTTTGGGATAAATAAGTAATTTTTATTCGCGTATGTAATA

AGTTTGAGATTTTGTAGAAAAACATGTTTTTACTATAAGAAGCATTTAGTTTATACTACTCCCTTACTCCGTTA

CAATTTGTTTGTTTGGTTTTGAATTGTCACGAGTTTTTAAAAAAGAGAGTAAAGAACGACTTTTGAATCTCAT

GGTCTTTAAACTAAAGAGATTGTGGGATGTACGGAATTTGGTCTTTTATCTTGTGCTATTAAATATGGTAGGT

GGAAAGTCGAATAGAAGAGTTGCCAAATAAGGAAAGAGACATTATTTTTGGAACAAACTAAAAAGAAAAGT

AGGATAAACAAATTAAAACAGGGGGAGTATTTGGTTTCTCATCGGTGCTACAAGAATTACTAAAAAGCTAGC

GTCTTGCCTTTTTTAAAAAGAAATTTTGATCCTGAAAGATGGAGTTTTTAATTTGAATATGGATGTCACTTGCT

AATTAGGTTCGAATTCTGTTCATTCGAAAGCTTGGAGCTTTTTACTTTGTTTATAACTACATAGTTGATTCTCT

ACACTTGTTAATGTTTCTCATCCTGTTGAGTTGATTGAAAATTTATGTTTTTTGGATAACATATTAATTGCTCTC

GTTCTCGTAAATGTCTAATTTCTGCATCAATTTTTGTTGTTTTATTCGTTGATTAGCTAATTCTTAGAAAATGTA

GTGTTCTGTGATGTGCGAAAGTAATCTATAAATAGTTAGACTCTAATCAGATTTGTGCTAAATTCTAGTTAAA

TTTGTCTAAATTGGCCTGAGATGAGTTTATATAAACTGTGGAGTTACATGGTCAGTGAGGATTCATTTATACG
```

-continued

ACCTGAACTTGCTTGGACTGAGGTGTTGTTGTTATTGTTGTTTGCTGAAATTGTGAATGACAATGTTACTATAA

GGAAAATGGATTTTGAGCATAGTGTGAGTCTCTACTGATTACACAGGTTGATAATAGTATTGTTATATTTGTTT

TGCTTAAAGCTTAGGGGAAGACTCTTTTTTAATGTTGAGAGCAACTTTCTTTTGCAAATTATGCTATGTGGGTC

TTTGCTGATTGTTAACACGGTTTAGCTTGTCACAACACAACCTACTGGAAGCTGGTTAAATTTTGCTTGTAATT

TCTTGTAGGAAGGTCCTGAGGGAAGCTGCTTCTGGAGGAAGAGATGCTGAACGAGTGAAACTGAAATTGGAA

ATTAAAGTTGAGGTAAGGATATATTAGACATCCAGCATCATTCAGTTGTGGGGTGCGGGCCTTGGTTAGAACT

TTGTTTTAGCTTCCAGCATAAGGTGTTTTAATATAAATTGAAAGATAAAACTTTGAAATCAATTAACTATAGA

GAAGAATCTACTAAGGATAGAGAGGAGACTTTTCTTTGTCTTCCTTTTCCAATGTGGTCGAGATGAAGTATTT

TTGGGCAGTTTGATGAATTTTGAGGATATCAATACAACCCGTGTATGACATATGCATGATAAATTGTCACATA

ACAATGCTCCATTTCTAACTAATCTCAATAAATGCGATGTTGATAGTTTTGTTACCATAGTAATGATGACAATT

GTAATGTGACTGGAAAGTAGGAAATAGATAGTGCTCTTTCTAGAGTTTTTATTTGAATATATTCCACTCCAAT

GTGGTATAATATAATCAATTTGGTGTTTTAGAATGTGGAGTATGACAAAGAAGGTTCTGCCTTGCGTATTCGC

GGGAAGAATATTCTGGAGAATGAACATGTAAAGGTGTGTATTCTTCAACTTAATCCTTTTGGATAAATTCCTA

ATATTGATGCTGCAACAAAAATGTATCTAATTATTTTATTGCAGATAGGGGCCTTTCACACTCTGGAAATTGA

GCAACACAGACCTTTTGTGCTAAGAAAGGTACAATGCTGTGTTTTGATTCTTTTGCAACTATCACTCTGTTTTC

TTTTAAAAATTTTGAGGTATATTATTTGCACTTTAAAAGCTATCAAGCTGGTGATATATGTTCTTTAGGATTGC

AGCTCTAACCTATGTTTCTCAGACTCTTCAAAAATGTCAACTGGTGCATGTCGGATTCTCCAAAAATAGCGTG

TTTTGGAATATCCGACATGGGTGCGGCATTGTAAGTGAAGAGTCCGCAACTTAGGCTCTAACAAGTAAAAAA

ATCTGTAAAGTTATTCATGTAATTTACATTATTATTATAAAATCCCCGGAAAAAGAAGAAGAGTACCTTTTTTT

TCTTTAATAACCTTGGTATCCGGGCCAGTTTGTGCACACTTCGACCCACTTCCACCAACACAGCTACCGCCTAC

AGGGTAACTCTTTCCATCAAGGTTTTGACAAATAAGAAGAAATTGTCTAGTGTTTTCGCCTCTGGTTGGATTT

GAACCTAAGATCTTATGACTCTTAACTCACTTCATTGGCCGCTAGACCATACCCCTTGGGTGCAGTTACTTGA

AACTAAGTTTAATTTTTCCCGCTAAATTTCAGTTGTCCCGCCGCTGACACCCCTTCGAGGCATCTCGTGTTCCT

GTCCTTTGACGTAGTTCACATCCTGCACGAAAGGTGTACATACGATACCTCCTTTCTGTCTCTAGATGGAACA

ACCCTTCTACATTAATGATGATTCCACCTTGGTTATCATCATGACTAATTCCATGCCAAATAAGCCAAGAAAT

AGCTACACATTTTCGGCACACACCAAAAAAGGGAACCCGAAGTATATTGTCGTTGATTTCTCATAAACAAGTG

TACAATGGTTCGAAAATTATCCGAAAGCATTAATGCTTATTAAGCTATTATTAACTCCTATATTATACATTCTA

TGGACTTTGGTCTGAGGGGGCTAGTTTCTTTTCTCAGCTTGTTTCTTTGTAGTTTGAAGGATCTATGCCCCCTA

GTTCGTCCAACACAGGTAGGGCTGAGGCATGATAAGATAAGTGACGGTTTGTGTAGCCTAGGTAATATATAC

TTAAGTGATGCAACAATATAAGTTCAGGTAGGGGAAATTCTTCTCGTACACATAGGAGTACATGGAATTTGGT

AAGATTTCTTGATTTTTTTCTGCATTATACAAAGTTGCTGCATAGATTAAGTATAACTAAATAAGTGTCTTTTT

ATAATTAGAGGCTAATGAGTCATAGAAGTTGAATTAGGAGATAATCATTTGTAGTTGTAACTAGAGGTTTCTA

TAGGGAAATTGAGGAGTATCCCAATCGAAATATAAATGCCTAAAAATGTCTGGGCTAAGAATTACATGTGAAC

TTGATGTCTGGGCTAAGAATTACATGTGAACTTGAAATTATATTGATCGGGTACAGGTCGAATGAAATTTTCC

ATAATTTCTTTTACTACTGGATTTATTACTTAAAAGGGTATAAACTTATCAAAATAAGATTTCTTAGAAGGTAT

GCGTGCTTTTATTTAAAACTTTTGTTTATGTATAATCCTATCTAATGCATGTACATGAATTATTTTGAATTTATT

TTTACTCAAAGTAATCGTTATTTTCCTGTGTCATCTTCCTTATTATTTTTGTATATTCTATTTGTTTAGCAAATAT

ATGAGCATCTTGTTTGTTTCAATCTTAGTCTTACCTGAACATAGTTGATTTATACGAAAGCTTATACATATATG

AGTTCTGACTTGCATTATCTGATTTAGGTGGTCTGGGACTCACTGGCACGGGAGGTTCTTCGTCAAGCTTCTGG

TATTTTTCACAGTGCACTTTAACAAAGTTATATTTTTATTTGTTCAAGTGTTGCCATTAACTTTATCTGCAATAT

-continued

```
TAGGCATTTTAGTTCATAGCCTGACTTTTCATCCATAACTTATCAAGTTCTATAACATGTTGCTGCTTCTTTTA

GTACATTGACATGATTGTGAAACCACTTTATAGGTGCATTATTCTTAGATGGATTGTTTCAGTCTAGGTGTCTT

TTAGCCCTTATGTTGCAGAGGTTTTCTTCTTTACTCGTACACTTGCAGTGAGAACATGATTATTCGCTGCAAGT

ACATGTGTGTTGCAGAGTGCTTTTGAACTGATGAGAAGTTTCCTATATAATTGTTGATATTCAGCTATATTGAT

TCCAACATGGATATGTGTTTGTAACTTTGTACTGCTCTTAGATTTACCGTTTCAATATGCTGAATACGGTTTTC

CTTTTTGATGATTCAGATCCATCTGCAAGTGCTGATCTGGCTGTGGTTCTGATGCAAGAAGGATTGGCACACA

TTCTTCTTATTGGTAAAAGGTAAGCTTGACAATCTCATAGTCCTATGAATACAAGTTTTAAACAGATCTTGAG

CATCTCCTTTTCTTGTATTTAAACGAGATGTAATAGTTTAAAAGTCGAATGATTATGTCAGAATTTCTATATGT

TGAGGCTGAGTTAAGTGTTAACTAGATTGTATGGCATAATTTTACCTTATGTACTTGTTACTGTTGTCTGAACA

GTGTGACTATCACCCGTTCTCGTATAGAGTCTTCTATACCGCGCAAGCATGGACCGGCTATTGCAGGTTATGA

TAAGGTGAGTCTCTTACTTCTTTTTGTTTCATCTTTTGTATAATTTAATTATTTTGAACATGACGTCAAGTGAAA

TTGTGTTCTTAATTTTGATTTGCAGGCGTTAAATAAATTCTTTGACAATGTTCTACAGGTAGACTTTTGTCAAC

TTTCTTGATGTTGCTTAATTTCCAGAAGCAATATGTTATAGGTTCTTATTTCTGTTGCAGGCCTTTGTCAAGCAT

GTTGATTTCAAAGTAGTTCGCTGTGCTGTGATTGCAAGTCCAGGATTCACCAAGGTATTTTTTGTATAGTTACA

CTTCTTAGCTAGTCATACTTTTATGCTATGTTACAAGGGGTAGAACTTGCATATCTAATTATATCTGTACTATG

CATATGTTAATTCAGTTGTGACATTTAAACTTTTTTGTGTTGAATGTGCAGGATCAGTTTCATCGTCACCTGTT

GTTGGAAGCCGAGAGGAAGCAACTAAGACCTATAATAGAAAATAAGTCACGCATAATTCTTGTCCATACAAC

CTCGGGATACAAGTATGCCCTTCTTTCTCTCTCCTTGCCCTTCATCTGACATCTCAAAACGAGTCAATACAT

TTTTGTGCAAACCATATGATGTTAGACATGCGTGCTAGTCTAAAATTGACTAATATGTAGCAATACATTTTGT

GTACGCGATTCTCTCGTCAGTACTGCTATTTTAGTACAAATCGCCTTTATTATTTGTCTATTGTAGTTGATATGT

AAAAGTTCAATTATTATCCAGCACGGGTGTTTAAGGCCGAGAGTTTTTTTTTCCCTCGTTTTACAGACATAGT

TTGAAAGAGGTTATGGATGCCCCAAATGTAATGACTATGATAAAAGATACAAAAGCTGCCAAAGAGGTACCT

TCTGACCCTTGTCCAACTTGATATGATCTTTAATCTTTATTCTTGTGTTTGTTCAAGTCTTTTTTCGTATTTTTG

GGAATAACTGTTTTCCTTTCTCTTCCAATCTTAATCAGGTTCAAGCCCTAAAGGATTTTTTCAACATGCTTTCA

AATGTTAGGTTCTATCCTTGGTCTCAATGTTCTATTTATATTTTTCTTAATAACTTTGGATGTTTCAGATTTTTA

TCTATCATATGCTAAGAGTAAACACAGATTGTTTGGTTTTGAATTTATTTGTTTGCTTTTTTTGGTGTTTATCGG

TTATCTTGGGTTCTGTAAGAGGCCTGAGAGTTTCAAATAAAAGTTTGAGGTGTTTAACTATGCATGACGGATA

TCCCTGTTTAAGGAGAGGTGGACTAATCTGAAATATTTCTAGATTAAGAACAGATACGTTGTGTTATGATGGG

CAGCTGGTGATATTGTTATCTCTGCGTGTGCCTTTTTTTAGGCCTTTCTACCAATTGAATGCTGAAAATTCATTT

GCAACCAACCTTGGTTGAATTTATTTTCAGCAAGGATCCGTCATAATTCTCAGATATCCAATCATCAACAACT

TTGAACTTCTATTAAATTTTAGGGCATCTCAGTTGTGTTCTTTCATCTTTTGATTTATATGCAATTTTACTGTA

GTAATAGGAGTATCTCTCTTCAATGCTTTGGCCATATCGGTACGAGAGAATTTATCATCTGATGTGCCCTCTCC

TTTACTTTTTTGCAGACAGAAAATACGATAAGGAAGTCTTAATTAAAAATATGCGTGTGCTTGATTTTCTGGTT

TTAAGGATATTTAGGTCTAAAAACTATAGTTACATTACATAATTTAGGGATGCTAGATGTAGAGGTCTTTTGC

TAGAGCGAGTGCTTGTTTGAACCCCCCGCCCCGCCCCGCATATTTCATGAATTATGATATTAATTGGATATTTA

TGATACCGCTTTTCAAGCTTTCTGAAGAAACTAAGAAGGATAACATCTTTATTTAAAAACTTTTTTCCCTCTCT

TGTTATAACTTCTTGCAATAAATGTAGTCATGTCCCTTTTTCTGGATCTCTTAACATTTATATTAATGAGCCCCT

GCATGAAGTTTACTTCCAGTTGTCAACAAATAGATCCTTGTAGTGTGTTTCTTTACCCGAAACTTGTGAAAATT

GAAGTTACTTTATTTGGACTTCTCTAGGATCCTGATCGTGCATGCTATGGACCAAAGCATGTTGAAGTTGCCC

ATGAGCGTCTGGCTATTCAGACACTTCTCATTACTGACGAGCTCTTTAGGTGAGTATCTTATGGTCCCAGGTTA

ATGGGGGCTTTATGAGCAATAAAATTAAACTGTATATAGCTTGATATAAATTTGCAACTCGTGGCATATTTCA
```

-continued

```
AGTTCATAAGTATCTCTTTTTACGTGCTTAGCTTTTAAAATCGACATCTTTGGTTCATAGGATAATATGTAAAC

ATGTATAACTATCTTCAAATCTCAACCAGTTATGTATGGGCCATTTCACTCGTGCTGTATATATATAGTTGGTT

GATATCGTACATGAGAAATATCCAACTTCTTTTGATCTGTTGACAGGAGTTCTGATGTAGAAACGAGGAAAAA

GTATGCTAATTTGGTCGATTCAGTCAAGGATTCAGGTGGTACTGCTCTCATTTTCTCGTCAATGCATGTCTCCG

GAGAACGTGAGTATATACAATTCCTGTTAATTTCTTTTTCCTCCCAGCATTTTCATCTCTGCCTTTCCCTGTCGC

CCCCTAGTAATGCTTAGAATGGTATTTTCCTTCTGTGCACATATTCATTGTCCCATAGTCGCTTCAAATCCTTTT

TCCTTCCTACGAACACACGTTCTTTACTGCATATTTGTCAAGGCTGATTAAAACAACTTTTGGTTTTCGTCACA

GAATTGAATCAGCTAACCGGCATTGCTGCAATCCTTCGTTTTCCTTTGCCGGAGCTGGAAGACATTGAGATGT

GA
```

Although the embodiments of the present invention have been shown and described, it is should be understood for those of ordinary skill in the art, various variation, modifications, substitutions, and improvements may be made to these embodiments without departing from the principle and spirit of the present invention, and the scope of the present invention is limited by the accompanying claims and their equivalents.

What is claimed is:

1. A method for creating a germplasm of a male sterile crop by a gene editing, comprising:
   (1) performing the gene editing on an exon region of a Ty-5 gene, wherein performing the gene editing comprises:
      (a) selecting gRNA target sites in the exon region of the Ty-5 gene by selecting an 18-20 bp upstream of a protospacer-associated motif (PAM) as the gRNA target sites, wherein the gRNA target sites are 5'-N18-20NGG-3', NGG is a PAM sequence, and N18-20 represents a recognition sequence of the 18-20 bp;
      (b) introducing a DNA sequence deletion on the exon region by using a repair mechanism of plants to double-strand breaks (DSBs),
   (2) assessing pollen content and germination of homozygous gene edited strains; and
   (3) selecting male-sterile strains.

2. The method according to claim 1, further comprising designing primers amplifying the gRNA target sites according to upstream and downstream sequences of the gRNA target site, extracting DNA of the regenerated plant, using the DNA as a template for a PCR amplification to obtain amplified products, sequencing the amplified products, and performing a sequencing analysis on the regenerated plant to determine whether the gene editing occurs and whether an editing type is a homozygous mutation.

* * * * *